United States Patent [19]

Herman

[11] 4,174,155

[45] Nov. 13, 1979

[54] SOUND ABSORBING ARTICLE AND METHODS OF CONSTRUCTING AND UTILIZING SAME

[76] Inventor: Sal Herman, 27096 Aberdeen, Southfield, Mich. 48076

[21] Appl. No.: 834,323

[22] Filed: Sep. 19, 1977

[51] Int. Cl.² .............................................. G02C 11/00
[52] U.S. Cl. ..................................... 351/158; 128/152; 181/18; 181/126
[58] Field of Search ................................ 351/123, 158

[56] References Cited

U.S. PATENT DOCUMENTS 3,856,007  12/1974  Leight .............................. 351/158 X

FOREIGN PATENT DOCUMENTS 563174  3/1957  Italy ........................................ 351/123

Primary Examiner—Paul A. Sacher
Attorney, Agent, or Firm—Irving M. Weiner; Pamela S. Burt; Melvin Yedlin

[57] ABSTRACT

A sponge sound absorbing article for placement on the side frames of eyeglasses for workers employed in very noisy environments. The sound absorbing article eliminates any sound gap between the sides of the eyeglass frames and conventional earmuffs to protect the ears from sustained exposure to dangerous noise levels.

8 Claims, 5 Drawing Figures

SOUND ABSORBING ARTICLE AND METHODS OF CONSTRUCTING AND UTILIZING SAME

The present invention relates generally to sound absorbing articles and methods of constructing and utilizing same.

In particular, the present invention relates to a sponge sound absorbing article for use on the side frames of eyeglasses to eliminate sound gaps between the side frames of the eyeglasses and conventional earmuffs normally worn by workers to protect the ears from sustained exposure to dangerous noise levels.

BACKGROUND OF THE INVENTION

Prior to the advent of the present invention, various attachments and adjuncts for eyeglasses have been attempted. The prior art is exemplified by Bussey U.S. Pat. No. 538,151 entitled "ATTACHMENT FOR SPECTACLE FRAMES"; Grier U.S. Pat. No. 2,031,771 entitled "TEMPLE FOR EYEGLASSES"; Sygnator U.S. Pat. No. 3,807,526 entitled "EAR PROTECTOR"; Leight U.S. Pat. No. 3,856,007 entitled "EAR PROTECTOR ASSEMBLY"; and Leight U.S. Pat. No. 3,943,925 entitled "EAR PROTECTOR ASSEMBLY."

The prior art arrangements have proven unsuccessful, cumbersome, expensive, and complicated, especially in connection with the situations outlined hereinbelow.

Workers who are employed in very noisy factories, such as stamping plants, are compelled to wear earmuffs to protect the ears from sustained exposure to dangerous noise levels. Such workers who also normally wear eyeglasses or safety glasses are unable to obtain proper sound sealing between the earmuffs and the eyglasses, and thus are exposed to dangerous noise levels because of sound penetrating through the gaps between the earmuffs and the sides of the eyeglass frames. The sound absorbing article of the present invention solves this problem in a most expeditious and inexpensive manner.

SUMMARY OF THE INVENTION

The present invention provides a sound absorbing article for use in conjunction with glasses for the eye, comprising first means for absorbing sound, and a channel provided in a first surface of the first means into which channel a frame member of such glasses may be disposed. There is also provided second means for adhesively securing at least a portion of the frame member to at least a portion of a second surface of the channel provided in the first surface of the first means. The second means is disposed within the channel provided in the first surface of the first means.

The present invention also provides a novel method of constructing and utilizing the aforementioned sound absorbing article.

It is an object of the present invention to provide a sound absorbing article which is first applied to eyeglasses or the like, and then the glasses are placed on the user, and thereover there is placed earmuffs.

Another object of the invention is to provide a sound absorbing article for use by workers employed in very noisy environments and factories, such as stamping plants, who are compelled to wear earmuffs to protect the ears from sustained exposure to dangerous noise levels.

Another object of the invention is to provide a sound absorbing article which is primarily made of sound absorbent sponge of the industrial type which is normally used for deadening sound around and on noisy machinery.

A further object of the invention is to provide a sound absorbing article which is provided with a channel or groove on one of its sides, and wherein there is adhesively affixed to the roof of such groove or channel a small strip of peel-off double-stick tape.

Yet another object of the invention is to provide a sound absorbing article which is employed and disposed as an intermediate member between eyeglasses and earmuffs.

The foregoing and other objects and advantages of the invention will become apparent from the ensuing disclosure in which several preferred embodiments of the invention are described in detail and illustrated in the accompanying drawings, in which like parts are designated by like reference numerals. It is contemplated that minor variations in structural features and arrangement of parts thereof may occur to the skilled artisan without departing from the spirit of the present invention and without sacrificing any of the advantages or objects of the present invention.

DETAILED DESCRIPTION

Before explaining the present invention in detail, it is to be understood that the present invention is not limited in its application to the details of construction and arrangement of parts as illustrated in the accompanying drawings, because the present invention is capable of other embodiments and of being practiced or carried out in various other ways. In addition, it is to be understood that the phraseology and terminology employed herein is for the purpose of description and illustration only, and not for the purpose of limitation.

Figure 1:
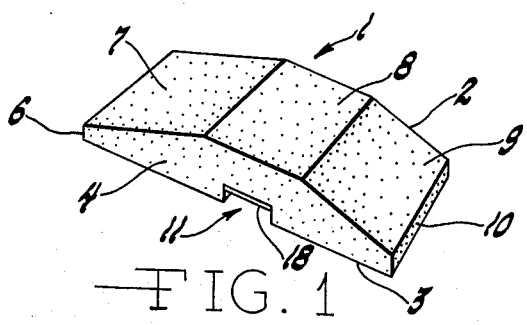
FIG. 1 illustrates a three-dimensional perspective view of a sound absorbing article in accordance with a first possible embodiment of the present invention.
Figure 3:
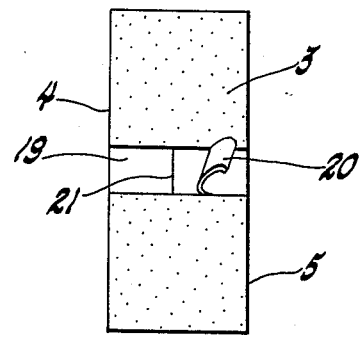
FIG. 3 illustrates a bottom view of the article shown in FIGS. 1 and 2 illustrating the peeling off of one-half of the double-stick tape.
Figure 2:
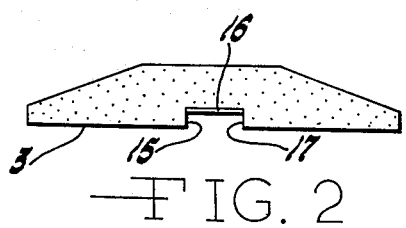
FIG. 2 illustrates a front elevational view of the sound absorbing article depicted in FIG. 1.

With reference to FIGS. 1, 2 and 3, there is shown a sound absorbing article 1 having first means, such as main body member 2, for absorbing sound. Preferably, main body member 2 is fabricated from sound absorbing sponge of the industrial type which is conventionally employed for deadening sound and noise around and on noisy machinery.

The main body member 2 may be provided with a substantially flat first surface 3 and a pair of substantially parallel surfaces 4 and 5 which are disposed substantially perpendicular to the first surface 3.

The remainder of the main body member 2 may have a generally convex configuration which may be arcuate in nature or may be formed from substantially flat surfaces 6, 7, 8, 9 and 10. A groove or channel 11 is provided in surface 3 into which channel 11 a side frame or temple bar member 12 or 13 (see FIGS. 4 and 5) of glasses 14 for the eye may be disposed.

Channel 11 includes a first surface 15, a second surface 16, and a third surface 17. Second surface 16 is disposed substantially parallel to surface 3 of the main body member 2. The article 1 includes second means, such as a strip of double-stick tape 18, for adhesively securing at least a portion of frame member 12 or 13 to at least a portion of surface 16 of channel 11. The tape 18 has one adhesive surface secured to channel surface 16, and has adhesive secured on its opposite surface and covered by peel-off members 19 and 20 separated by a score line 21.

Figure 4:
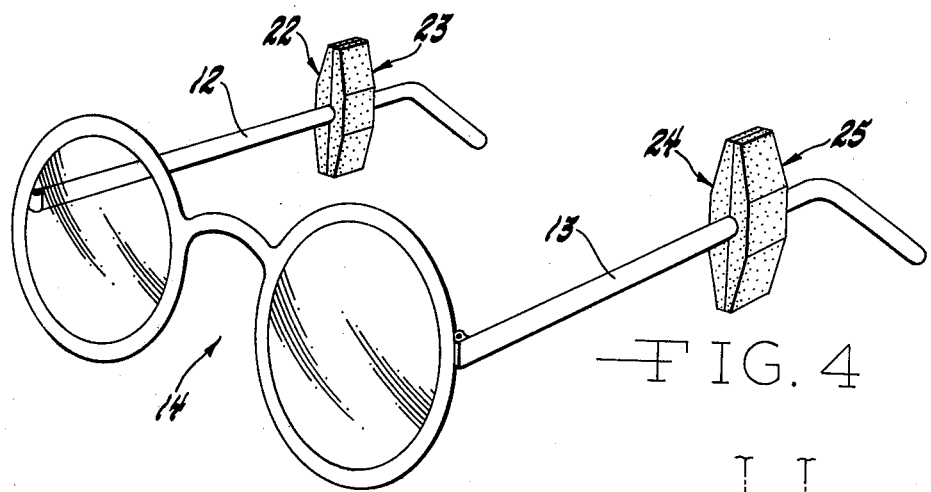
FIG. 4 illustrates a three-dimensional perspective view of four of the FIG. 1 articles applied to a pair of eyeglasses.

With reference to FIG. 4, there is shown four sound absorbing articles 22, 23, 24 and 25 each of which is similar to the sound absorbing article 1 illustrated in FIGS. 1, 2 and 3.

Figure 5:
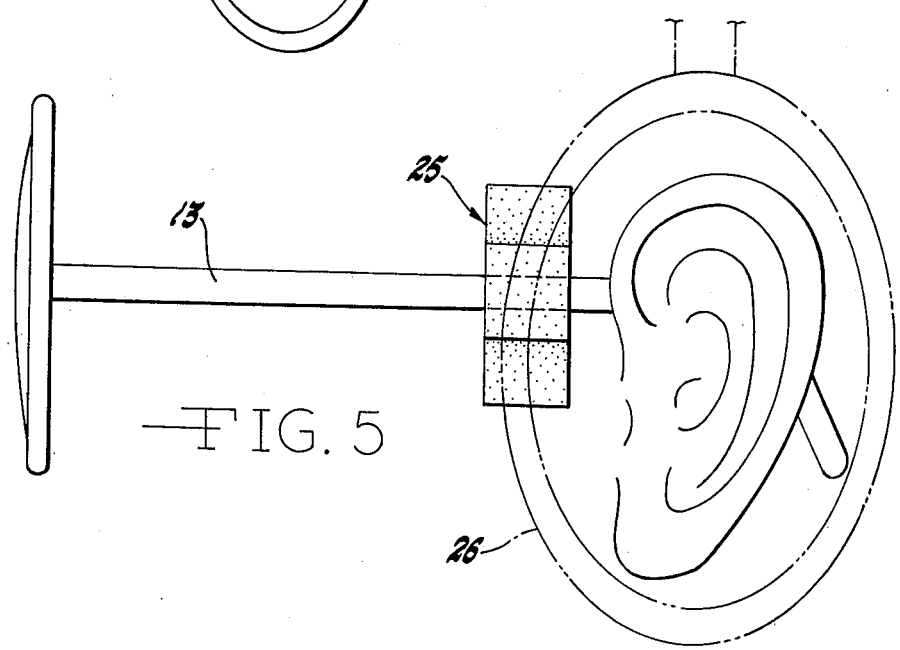
FIG. 5 illustrates a side elevational view of the sound absorbing article as applied to eyeglasses and as used by a wearer in conjunction with earmuffs.

To use the articles 22, 23, 24 and 25, the user merely peels off the outer protective covering layer consisting of peel-off members 19 and 20 of the double-stick tape 18, which may optionally have a central break line or score line 21 to facilitate peeling off the covering. The exposed outer adhesive surface of the tape 18 is then applied to the eyeglass side frame 12 or 13 which is inserted in the channel 11. Four such sound absorbing articles 21–25 are normally used, with two such articles surrounding each of the eyeglass side frames 12 and 13 as depicted in FIG. 4. Optionally, where the eyeglasses fit snugly enough to the head of the user, it is only necessary to use two of such sound absorbing articles, such as articles 22 and 25, with one such article on each outside surface of the eyeglass side frames. The user first applies the sound absorbing articles to the eyglass side frames, places the eyeglasses with sound absorbing article fixed thereto on his head, and thereover places the conventional earmuffs, such as the earmuff 26 as illustrated in FIG. 5.

The sound absorbing articles thus serve to fill the gaps which would otherwise be present between the earmuffs and the eyeglass side frames, and between the eyeglass side frames and the side of the head of the user. Such otherwise-present gaps are extremely dangerous when the person is exposed to sustained dangerous noise levels.

The peel-off covering or coverings of the tape 18 facilitate the packing, shipping and storing of the articles before they are actually used. Also, this ensures an excellent adhesive quality to the tape 18 after the peel-off covering or coverings are removed. Optionally, a double-stick tape 18 without any peel-off protective strips may be used. Also, the invention contemplates a tape 18 which has a peel-off protective covering strip, but which lacks the break line or score line 21 which merely facilitates removing the protective covering strip.

Preferably, the material for the main body member 2 is completely porous, resilient, elastic, and an excellent sound absorber, such as sponge. However, the present invention also embraces any other suitable sound absorbing material for the fabrication of the main body member 2. It is also preferable that the sound absorbing articles include no rigid or inflexible portions or components.

As an alternative to use of the tape 18, the invention also contemplates and embraces the application of a pressure-sensitive adhesive in the channel 11.

While the main body member 2 may take various configurations and shapes such as the arcuate or curved shape mentioned hereinabove, an actual working embodiment of the present invention has employed the twelve-sided configuration illustrated in the accompanying drawings.

I claim:

1. A sound absorbing article for use in conjunction with an eyeglass frame having a pair of temple bar members, comprising:
   a main body member fabricated of substantially porous, resilient, flexible, and non-rigid sound absorbing material;
   said main body member including a channel formed in a first surface thereof, within which channel a temple bar of said eyeglass frame may be disposed;
   adhesive means for securing a second surface of said channel of said main body member to at least a portion of a temple bar of said eyeglass frame; and
   said adhesive means being disposed within said channel provided in said first surface of said main body member.

2. A sound absorbing article according to claim 1, wherein:
   said first surface of said main body member is disposed substantially parallel to said second surface of said channel.

3. A sound absorbing article according to claim 1, wherein:
   said adhesive means comprises tape having an adhesive surface on each of its opposed, parallel major longitudinal surfaces.

4. A sound absorbing article according to claim 1, wherein:
   said main body member is dimensioned so as to substantially fill the gaps between the temple bars of said eyeglass frame and a pair of earmuffs when said eyeglass frame and said earmuffs are positioned on the head of the user of said article; and
   at least one said sound absorbing article is disposed between each temple bar member of said eyeglass frame and said earmuffs.

5. A sound absorbing article according to claim 4, wherein:
   each said temple bar member of said eyeglass frame is disposed between two said sound absorbing articles which have their channels facing towards each other and which have said first surfaces thereof in intimate contact with each other.

6. A sound absorbing article according to claim 1, wherein:
   said main body member is fabricated from sponge.

7. A sound absorbing article according to claim 1, wherein:
   said main body member has a generally convex configuration.

8. A sound absorbing article according to claim 7, wherein:
   said main body member includes twelve substantially flat sides; and
   said main body member is dimensioned so as to substantially fill the gap between the temple bar of said eyeglass frame and the side of the head of the user of said article.

* * * * *